United States Patent [19]

Nakamura et al.

[11] Patent Number: 5,065,764
[45] Date of Patent: Nov. 19, 1991

[54] ULTRASONIC DOPPLER BLOOD FLOW VELOCITY DETECTION APPARATUS

[75] Inventors: Yasuhiro Nakamura, Tokyo; Ikuo Sakai, Kawasaki; Masami Kawabuchi, Yokohama, all of Japan

[73] Assignee: Matsushita Electric Industrial Co., Ltd., Japan

[21] Appl. No.: 452,653

[22] Filed: Dec. 19, 1989

[30] Foreign Application Priority Data

Dec. 21, 1988 [JP] Japan ................. 63-322655

[51] Int. Cl.⁵ ................................. A61B 8/06
[52] U.S. Cl. ........................... 128/661.09; 73/861.25
[58] Field of Search .................. 128/661.09; 73/861.25

[56] References Cited

U.S. PATENT DOCUMENTS

| | | | |
|---|---|---|---|
| 3,798,590 | 3/1974 | Jacobson et al. | 343/5 DP |
| 4,265,126 | 5/1981 | Papadofrangakis et al. | 128/661.09 |
| 4,334,543 | 6/1982 | Fehr | 128/661.09 |
| 4,612,937 | 9/1986 | Miller | 128/661.09 |
| 4,751,847 | 6/1988 | Katokura et al. | 128/661.09 X |
| 4,883,060 | 11/1989 | Pesque et al. | 128/661.09 X |

FOREIGN PATENT DOCUMENTS 0266998 5/1988 European Pat. Off. .
3614688 10/1986 Fed. Rep. of Germany .

OTHER PUBLICATIONS

Medical Electronics vol. 11, No. 3 (1976) pp. 65–71.
Brandestini, M., "Topoflow–A Digital Full Range Doppler Velocity Meter", IEEE Transactions on Sonic and Ultrasonic vol. 5425 No. 5.

Primary Examiner—Francis Jaworski
Attorney, Agent, or Firm—Lowe, Price, LeBlanc & Becker

[57] ABSTRACT

An ultrasonic Doppler blood flow velocity detection apparatus comprises: a signal producing circuit for producing trigger pulses, a sampling clock signal having a given phase relation with the trigger pulses, and a pair of quadrature signals of a given frequency in response to the trigger pulses. A transducer transmits also receives ultrasonic waves in response to the trigger pulses; The transducer also receives ultrasonic waves reflected back by an ultrasonic-wave reflective object and converts the received ultrasonic waves into an electric echo signal. A Doppler shift detection circuit, responsive to the pair of quadrature signals and the echo signal, detects the Doppler shift. An averaging circuit, responsive to the sampling clock, and the Doppler shift; averages plural time-different values of the Doppler shift, thereby producing a signal indicative of flow velocity of the ultrasonic-wave reflective object. The detection apparatus may further comprise a weighting circuit responsive to the output of the Doppler detection circuit and the sampling clock signal for weighting every value of the plural time-different values.

6 Claims, 7 Drawing Sheets

ULTRASONIC DOPPLER BLOOD FLOW VELOCITY DETECTION APPARATUS

BACKGROUND OF THE INVENTION

1. Field of the Invention

This invention relates to an ultrasonic Doppler blood flow velocity detection apparatus.

2. Description of the Prior Art

An ultrasonic Doppler blood flow velocity detection apparatus is used for detecting blood flow velocity which can be used in diagnosis. There are many types of Doppler blood flow detection apparatus utilizing the Doppler effect through reflection of ultrasonic waves. The ultrasonic Doppler blood flow velocity detector can select a portion where blood flow is to be detected with respect to distance and direction.

The most popular ultrasonic Doppler blood flow velocity detection apparatus detects blood flow velocity as follows:

Such an ultrasonic Doppler blood flow velocity detection apparatus transmits an ultrasonic-wave pulse whose center frequency is "f", at a predetermined interval into the human body by a transducer; then it receives a reflected signal, i.e., an echo signal, from a moving reflective object, such as a blood corpuscle; and detects the amount of phase shift of the echo signal, i.e., Doppler shift. An output signal of the phase shift amount, i.e. Doppler signal, indicates blood flow velocity.

In this conventional Doppler blood flow velocity detection apparatus, the relation between a shift frequency fd of a Doppler signal and blood flow velocity V is given by:

$$fd = (2V/c)fc \cdot \cos\theta \tag{1}$$

where fc is a frequency of ultrasonic waves; "c" is a sound velocity in the human body; and $\theta$ is an angle made between the ultrasonic transmitting direction and the direction of blood flow.

Structure described in "MEDICAL ELECTRONICS" Vol 11, No. 3, 65, 1976 is generally known which utilizes the above-mentioned principle. Hereinbelow will be described the above-mentioned prior art ultrasonic Doppler blood flow velocity meter generally with reference to FIG. 12 drawings.

Figure 12:
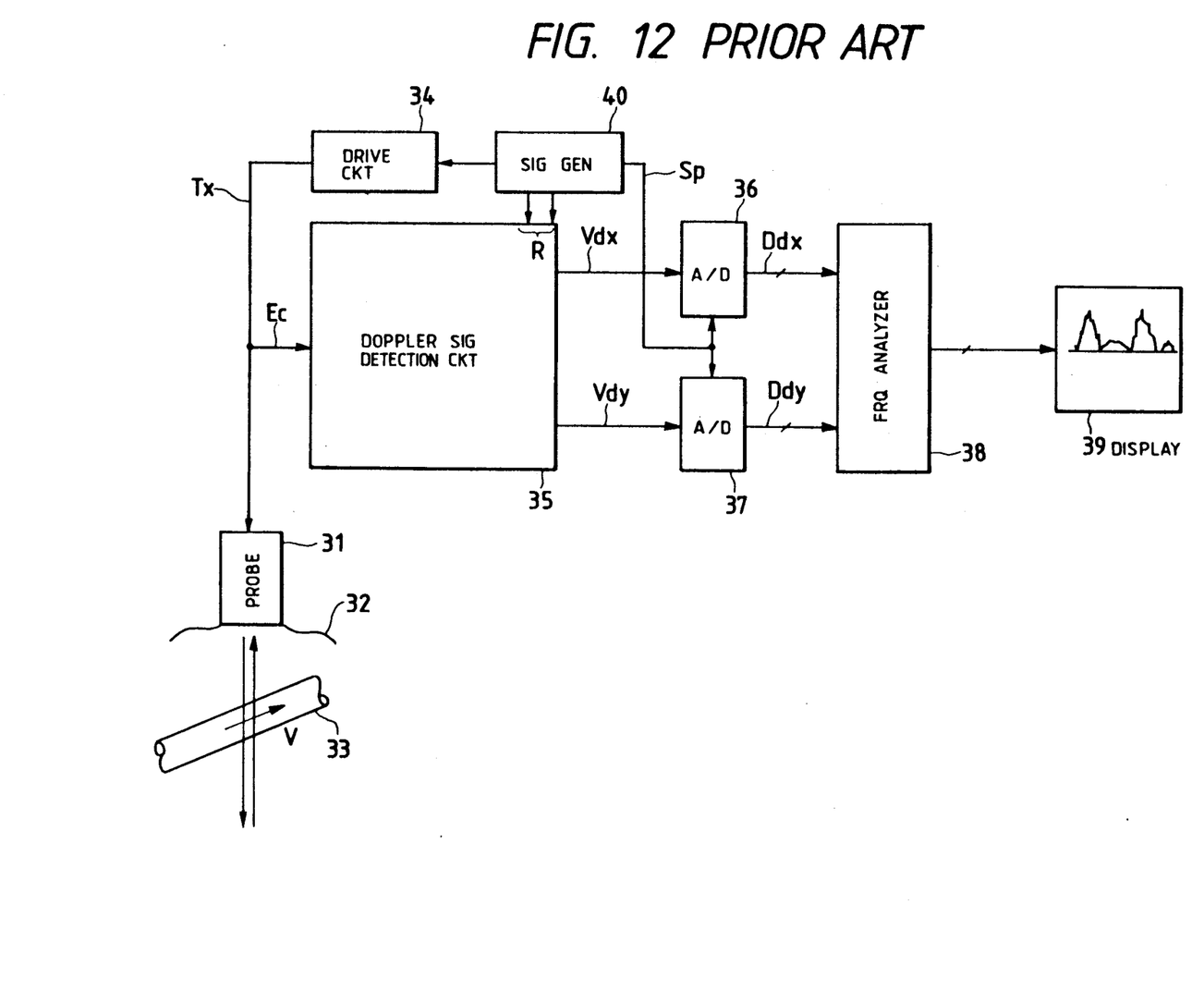
FIG. 12 is a block diagram of an ultrasonic blood flow velocity detection apparatus of prior art.

FIG. 12 is a block diagram showing structure of a prior art ultrasonic Doppler blood flow velocity detecting apparatus. In FIG. 12, numeral 31 is an ultrasonic-wave probe generally comprising a piezoelectric device for transmitting ultrasonic waves into a human body 32 and for receiving an echo signal from the human body 32, which is used for obtaining blood-flow information of the blood flowing in vessel 33 at velocity V. Numeral 34 is a driving circuit for producing transmission signal Tx for generating ultrasonic wave by the ultrasonic-wave probe 31. Numeral 35 is a Doppler signal detecting circuit for quadrature-detecting the echo signal Rx received by the ultrasonic-wave probe 31 to output quadrature Doppler signals Vdx and Vdy. Numerals 36 and 37 are A/D converters respectively for A/D converting the quadrature Doppler signals Vdx and Vdy into quadrature Doppler signals Ddx and Ddy of the form of numerical value. Numeral 38 is frequency analyzer for frequency analyzing the quadrature Doppler signals Ddx and Ddy through a calculating method, for example, fast Fourier transformation method (FFT). Numeral 39 is a display for indicating frequency of Doppler signals in the form of sonogram. Numeral 40 is a control circuit for controlling the drive circuit 34, Doppler signal detection circuit 35, and A/D converters 36 and 37.

Hereinbelow will be described operation of the above-mentioned prior art apparatus.

The drive circuit 34 generates transmission signal Tx in response to a control signal from the signal generation circuit 40, which transmits ultrasonic waves into the human body 32 through the ultrasonic-wave probe 31. The ultrasonic waves propagating through the human body 32 are reflected by the blood and return to the piezoelectric device of the ultrasonic probe 31 with a delay time proportional to depth of the portion where the ultrasonic waves are reflected. If the reflective object moves, the echo signal is subjected to Doppler effect with Doppler shift frequency fd in accordance with the relation of the above-mentioned Eq. (1). Frequency of the echo signal received by the ultrasonic-wave probe 31 is fc+fd by Doppler effect. The echo signal is quadrature-detected with quadrature reference signals R of frequency fc by the Doppler signal detecting circuit 35 to output Doppler signals Vdx and Vdy. These Doppler signals Vdx and Vdy have quadrature relation to each other and are of frequency fd which is obtained from difference between frequency fc+fd of the echo signal Ec and frequency fc of the quadrature reference signal. The A/D converters 36 and 37 sample in response to a sampling clock signal Sp sent from the control circuit 40 and A/D-converts the Doppler signals Vdx and Vdy to send digital values Ddx and Ddy to the frequency analyzer 38. The frequency analyzer 38 performs frequency of plural values of equally spaced points of the Doppler signals Ddx and Ddy through FFT method, etc. and indicates the result on display 39, such as television display to provide diagnosis data.

However, in the above-mentioned prior art ultrasonic Doppler blood flow velocity detection apparatus, there is a problem as follows:

Recently, attempts were made to use the ultrasonic Doppler blood flow velocity detection apparatus for diagnosis of blood flow whose velocity is relatively low such as that of the vessel of the abdomen or capillary. An, extremely high signal to raise (SN) ratio is required for circuits used in the above-mentioned apparatus, because these blood flows are very thin compared with arteries and veins of the heart or its peripheral portion so that magnitude of Doppler signal obtained therefrom is extremely small. Such apparatus cannot be realized. Moreover, when low velocity blood flow is detected, in the frequency analyzer 8 using the FFT method, etc. the number of analyzing points of the data is $Z^n$ ($n=1, 2, 3, \ldots$) and generally constant. Thus, resolution of low frequency components is increased by lowering sampling frequency of Doppler signal. Lowering the sampling frequency, decreases the Nyquist frequency fnq so that overlap occurs if Doppler frequency fd exceeds the Nyquist frequency fnq; Therefore, when attempting to observe flow components of low velocity among a variety of velocity components of a blood flow, the observation of the low velocity components is disturbed due to overlap caused by the high velocity components.

SUMMARY OF THE INVENTION

The present invention has been developed in order to remove the above-described drawbacks inherent to the conventional ultrasonic Doppler blood flow velocity detection apparatus.

According to the first embodiment of the present invention there is provided an ultrasonic Doppler blood flow velocity detection apparatus which comprises a signal producing circuit for producing trigger pulses and a sampling clock signal having a given phase relation with the trigger pulses; In response to the trigger pulses, the signal producing circuit also generates a pair of quadrature signals of a given frequency in response to the trigger pulses. This embodiment further includes a transducer for transmitting ultrasonic waves in response to the trigger pulses and for receiving ultrasonic waves reflected at an ultrasonic-wave reflective object and converting the received ultrasonic waves into an electric echo signal. A Doppler shift detection is responsive to the pair of quadrature signals and the echo signal for detect Doppler shift. An averaging circuit responds to the sampling clock and the Doppler shift by averaging plural time-different values of the Doppler shift, thereby producing a signal indicative of the flow velocity of the ultrasonic-wave reflective object.

According to the present invention there is also provided a second similar apparatus which further comprises a weighting circuit responsive to the output of the Doppler detection circuit and the sampling clock signal for weighting every value of the plural time-different values in accordance with predetermined weighting coefficients.

BRIEF DESCRIPTION OF THE DRAWINGS

The objectives and features of the present invention will become more readily apparent from the following detailed description taken in conjunction with the accompanying drawings in which.

The same or corresponding elements or parts are designated at like references throughout the drawings.

DETAILED DESCRIPTION OF THE INVENTION

Hereinbelow will be described an ultrasonic Doppler blood flow velocity detection apparatus of a first embodiment of the invention with reference to drawings.

Figure 1:
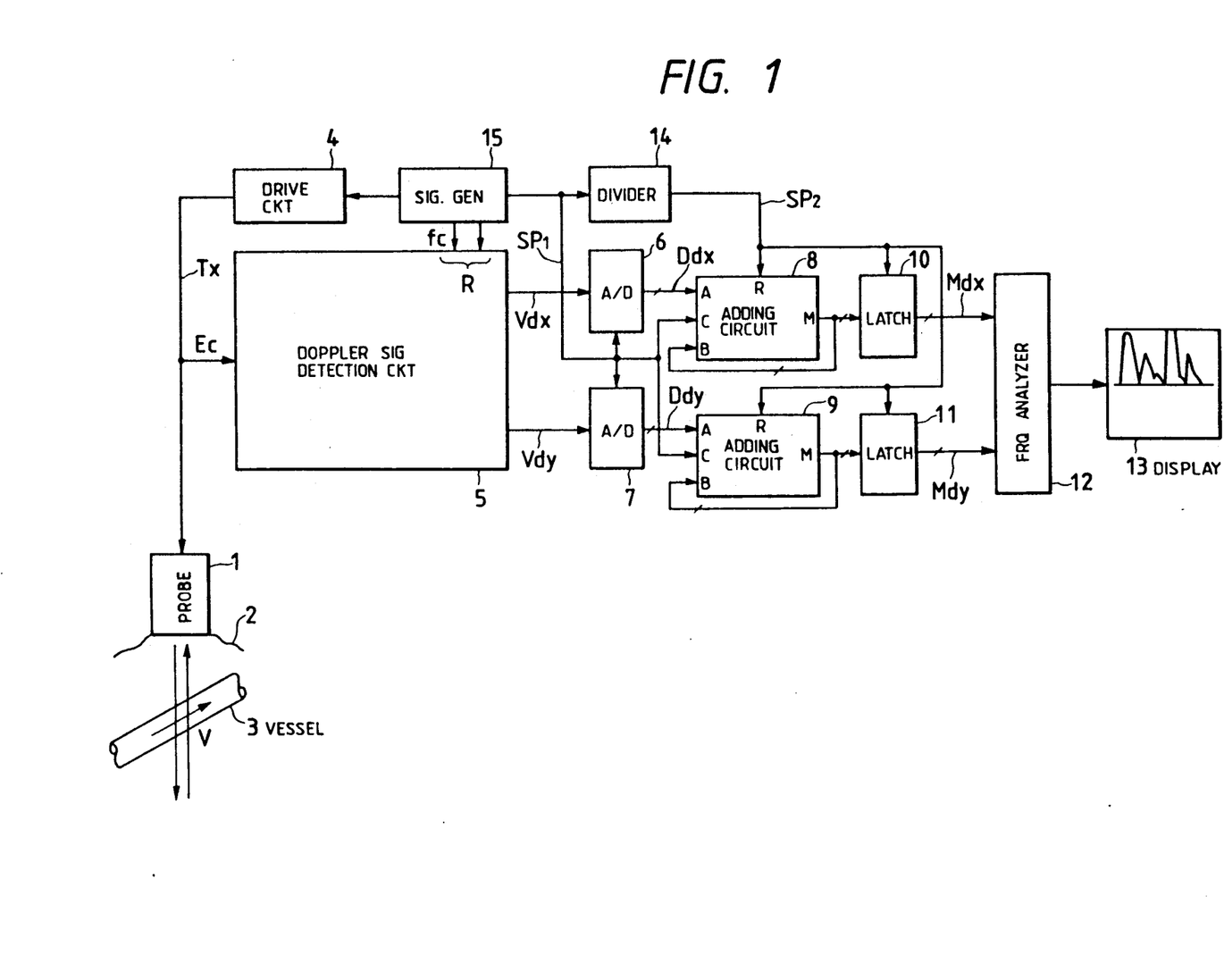
FIG. 1 is a block diagram of an ultrasonic blood flow velocity detection apparatus of a first embodiment of the invention.

FIG. 1 is a block diagram of an ultrasonic Doppler blood flow meter. In FIG. 1, numeral 1 is an ultrasonic-wave probe generally comprising an unshown piezoelectric transducer for transmitting ultrasonic waves into a human body 2 and for receiving an echo signal from the human body 2, which is used for obtaining information of blood flowing in a vessel 3 at velocity V. Numeral 4 is a driving circuit for producing transmission signal Tx. The transmission signal Tx is sent to an ultrasonic-wave probe 1 which generates ultrasonic waves in response to the transmission signal Tx. The ultrasonic waves transmitted from the probe 1 are reflected by the blood in the human body 2. The probe 1 receives reflected ultrasonic waves as echo signal. Numeral 5 is a Doppler signal detecting circuit for performing quadrature-detection of the echo signal Ec received by the ultrasonic-wave probe 1 to output quadrature Doppler signals Vdx and Vdy. Numerals 6 and 7 are A/D converters respectively for A/D-converting quadrature Doppler signals Vdx and Vdy into quadrature Doppler signals Ddx and Ddy of numerical forms. Numerals 8 and 9 are adding circuits for accumulating plural sets of sampled values of Doppler signals Ddx and Ddy to determine a mean value or average value, the number of the sets being predetermined. Numerals 10 and 11 are latches for holding added results from adding circuits 8 and 9. Numeral 12 is a frequency analyzer for frequency-analyzing the averaged Doppler signals Mdx and Mdy. Numeral 13 is a display for indicating the result of frequency analyzing in the form of sonograph. Numeral 14 is a frequency divider for dividing a first sampling clock SP1 generated by a signal generator 15 to produce a second sampling clocks SP2. The signal generator 15 produces repetition trigger pulses, quadrature reference signals rx and ry, and a first sampling clock SP1. The trigger pulses are sent to the drive circuit 4 to produce the transmission signal Tx. The quadrature reference signals rx and ry are sent to the Doppler signal detection circuit 5. The first sampling clock SP1 is sent to A/D converters 6 and 7, adding circuits 8 and 9, and divider 14.

Hereinbelow will be described operation of the above-mentioned ultrasonic Doppler blood flow velocity detection apparatus.

The drive circuit 4 generates the transmission signal Tx in response to the repetition trigger pulses from the signal generator 15. The transmission signal Tx is sent to the ultrasonic-wave probe 1 which transmits ultrasonic waves into the human body 2 by the unshown piezoelectric transducer of the ultrasonic-wave probe 1. The ultrasonic waves are reflected at the blood in the blood vessel of the human body 2. The reflected ultrasonic waves returns to the piezoelectric transducer of the ultrasonic probe 1, as an echo signal. If the echo signal received by piezoelectric device is subjected to Doppler effect, its frequency becomes fc+fd. The echo signal is converted into electric echo signal Ec which is sent to the Doppler signal detection apparatus. The echo signal Ec is quadrature-detected with a quadrature reference signals rx and ry of frequency fc by the Doppler signal detection circuit 5 which outputs Doppler signals Vdx and Vdy. These Doppler signals Vdx and Vdy have a quadrature relationship to each other. Therefore, the Doppler signal detection circuit 5 produces a difference frequency signal of frequency fd between the echo signal Ec, i.e., of frequency fc+fd and the quadrature reference signal of frequency fc. The A/D converters 6 and 7 sample Doppler signals Vdx and Vdy in response to the first sampling clock SP1 sent from the signal generator 15 and converts the Doppler signals Vdx and Vdy into digital values. The frequency divider 14 divides the first sampling clock SP1 to send the second sampling clock SP2 to reset inputs R of adding circuit 8 and 9 and latch clock inputs of the latches 10 and 11. The adding circuits 8 and 9 add A-input value to B-input value to output an added value at M output in response to the first sampling clock SP1 incoming to C input. These added values are latched by the latches 10 and 11 in response to the second sampling clock SP2. The latched signals are sent to the frequency analyzer 12. The frequency analyzer 12 performs frequency analyzing the Doppler signals Mdx and Mdy through FFT (fast Fourier transformation). The analyzed result is displayed on the display 13.

Figure 2:
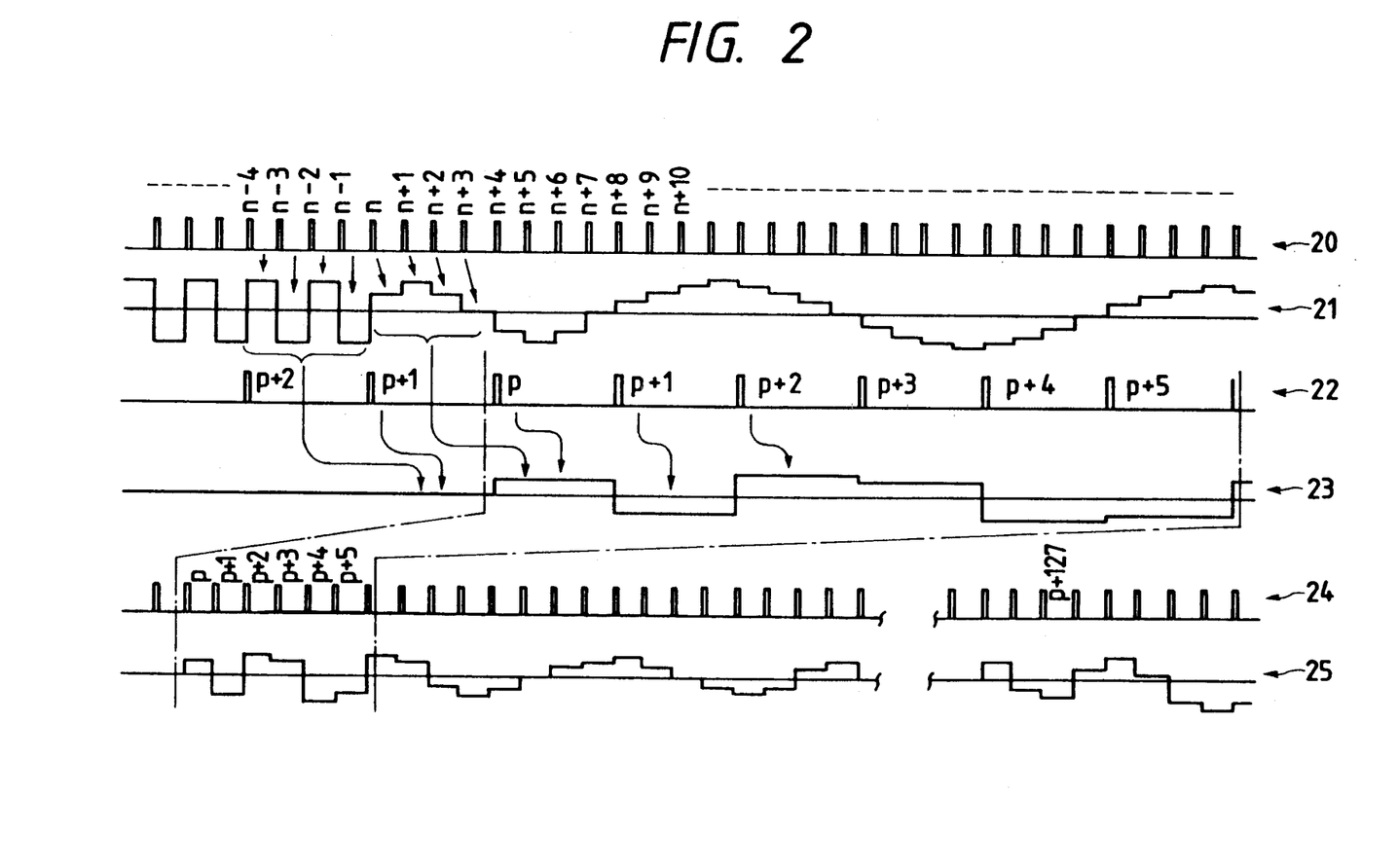
FIG. 2 shows a time chart for explaining operation of the first embodiment.
Figure 8A:
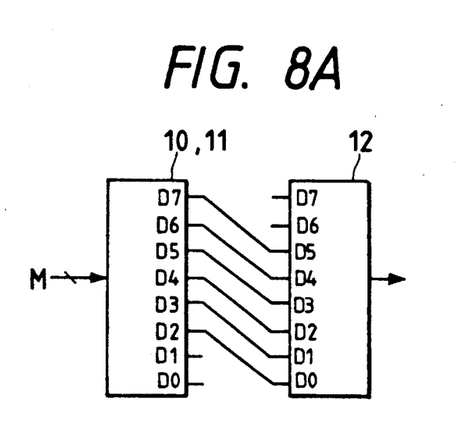
FIG. 8A is a block diagram of a bit-shift circuit of first embodiment.
Figure 8B:
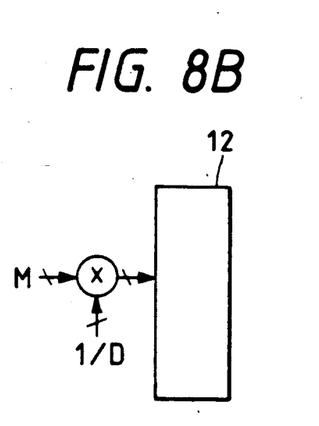
FIG. 8B is a block diagram of another bit-shift circuits of first embodiment.

More specifically, assuming that dividing ratio of the frequency divider 14 is ¼, the Doppler signals are processed as shown in a time chart of FIG. 2. In FIG. 2, waveform 20 shows the sampling clock SP1; waveform 21, Doppler signal Ddx or Ddy outputted from the A/D converters 6 and 7; waveform 22, the sampling clock SP2; waveform 23, Doppler signal mean values Mdx or Mdy outputted from the latches 10 and 11; waveform 24, a clock obtained from the second sampling clock SP2 by time-contraction; waveform 25, Doppler signal mean values Mdy or Mdy where waveforms 24 and 25 are indicated with time base contracted for convenience. At first, Doppler signals Ddx(n) and Ddy(n) obtained at $n^{th}$ pulse of the first sampling clock SP1 are applied to A-inputs of the adding circuits 8 and 9 and added to the value of B-input value respectively. The result of each adding circuit is outputted from M output in response to $(n+1)^{th}$ pulse of the first sampling clock SP1 applied to C-input. Here, the initial value of B-input is zero. At the same time, subsequent Doppler signals Ddx(n+1) and Ddy(n+1) are outputted from the A/D converters 6 and 7 in response to $(n+1)^{th}$ pulse of the first sampling clock SP1 and applied to A-input of the adding circuits 8 and 9 respectively. The next $(n+1)^{th}$ data are added to the result of $n^{th}$ data. At next $(n+2)^{th}$ of the first sampling clock SP1, A-input and B-input values of the adding circuits 8 and 9 are added to output at M-output and to be applied to B-input. At $(n+4)^{th}$ pulse, i.e., $P^{th}$ pulse, M-output is latched and the adding circuits 8 and 9 are reset. Therefore, all Doppler signals of $n^{th}$ to $(n+3)^{th}$ pulse of the first sampling clock SP2 are added and the result is outputted at M-output and held at $p^{th}$ pulse of the divided second sampling clock SP2 by the latches 10 and 11. If outputs of the latches 10 and 11 are shifted by two bits in the low-digit direction before these outputs are applied to the frequency analyzer 12, as shown in FIG. 8A or 8B, the result shows one fourth of the input value. These results are Doppler mean values Mdx and Mdy. In this case, if the number of input digit of the frequency analyzer 12 is large enough, it is not necessary to shift the value. Mean values Mdx and Mdy of the next Doppler signals which are obtained at $(n+4)$ to $(n+7)^{th}$ pulses of the first sampling clock are applied to the frequency analyzer 12. Subsequent Doppler signals are processed to determine a mean value continuously at every predetermined interval from a given number of Doppler signal values, as shown by waveforms of 24 and 25. If the frequency analyzer 12 performs FFT operation at 128 sampling points, in one analyzing operation, from $P^{th}$ to $(p+127)^{th}$ are used. As shown in FIG. 2, determination of mean values of given number improves SN ratio with respect to random noise such that SN ratio after averaging $N^{\frac{1}{2}}$ times that of a non-averaged value where N is the number of sampling points of Doppler signals Ddx and Ddy. In the above-mentioned example, since N=4, SN ratio becomes twice that of non-averaged value. Moreover, lowering sampling frequency increases frequency of limit where overlap begins to occur. For example, since the first sampling clock SP1 has higher frequency than that of the second sampling clock SP2, data before $n-1^{th}$ sampling are attenuated by averaging so that overlap is eliminated. Therefore, there are two limits in the ultrasonic Doppler blood flow velocity detection apparatus of the invention. The first limit lies in the second sampling clock SP2 of frequency f2, given by:

$$fd \leq f2/2$$

Therefore, Doppler signal higher than this frequency cannot be indicated. Under this condition, no overlap occurs. The second limit of frequency f1 of the first sampling clock SP1 is given by:

$$fd \leq f1/2$$

Therefore, Doppler signal frequency higher than this frequency produces overlap and thus disturbs the observation. Accordingly, sufficiently higher frequency of the frequency f1 of the first sampling clock SP1 increases the advantageous effect of the invention.

In the ultrasonic Doppler blood flow velocity detection apparatus using continuous waves, because Doppler signal is obtained continuously, it is possible to set the first sampling clock SP1 extremely high. On the other hand, the second sampling clock SP2 is selected in accordance with flow velocity. In the ultrasonic Doppler blood flow detection apparatus using pulse-like waves, frequency of the first sampling clock SP1 is equal to repetition frequency of transmitting and receiving of ultrasonic-wave pulses, which is determined by distance to the portion to be measured and propagation velocity of ultrasonic waves. The frequency of the second sampling clock SP2 is determined in accordance with blood flow velocity.

As mentioned above, in the above-mentioned embodiment, the Doppler signal detected by the Doppler detection circuit 5 is sampled at A/D converters 6 and 7; a mean value is determined from data of $n^{th}$ to $(n+m)^{th}$ sampling by the averaging circuit comprising a divider 14, adding circuits 8 and 9, latches 10 and 11 as $P^{th}$ mean value, as shown in the waveforms 21-23; and the frequency analyzer 12 performs frequency analyzing using from $P^{th}$ to $P+Q^{th}$ mean values determined similarly. As mentioned above, averaging adjacent plural data can suppress noise components and thus provide high SN ratio. Moreover, low-velocity blood flow can be observed clearly with high SN ratio because overlap does not adversely affect low-velocity blood flow measuring, for it is possible to attenuate a Doppler signal whose cycle is shorter than that of two sets of data respectively sampled at $n^{th}$ and $(n+m)^{th}$ pulses. The averaging circuit functions as a low-pass filter means. More specifically, noise components are cancelled when these components are accumulated by the adding circuits 8 and 9 because noise components occur at random and are sinusoidal components. On the other hand, low-velocity components of Doppler signal whose frequency is lower than f1 but higher f2, does not decrease when accumulating.

Moreover, it is possible to calculate a weighted mean value instead of above-mentioned arithmetic mean value.

More specifically, the signal generating circuit 15, Doppler signal detection circuit 5, adding circuits 8 and 9 are described.

Figure 3:
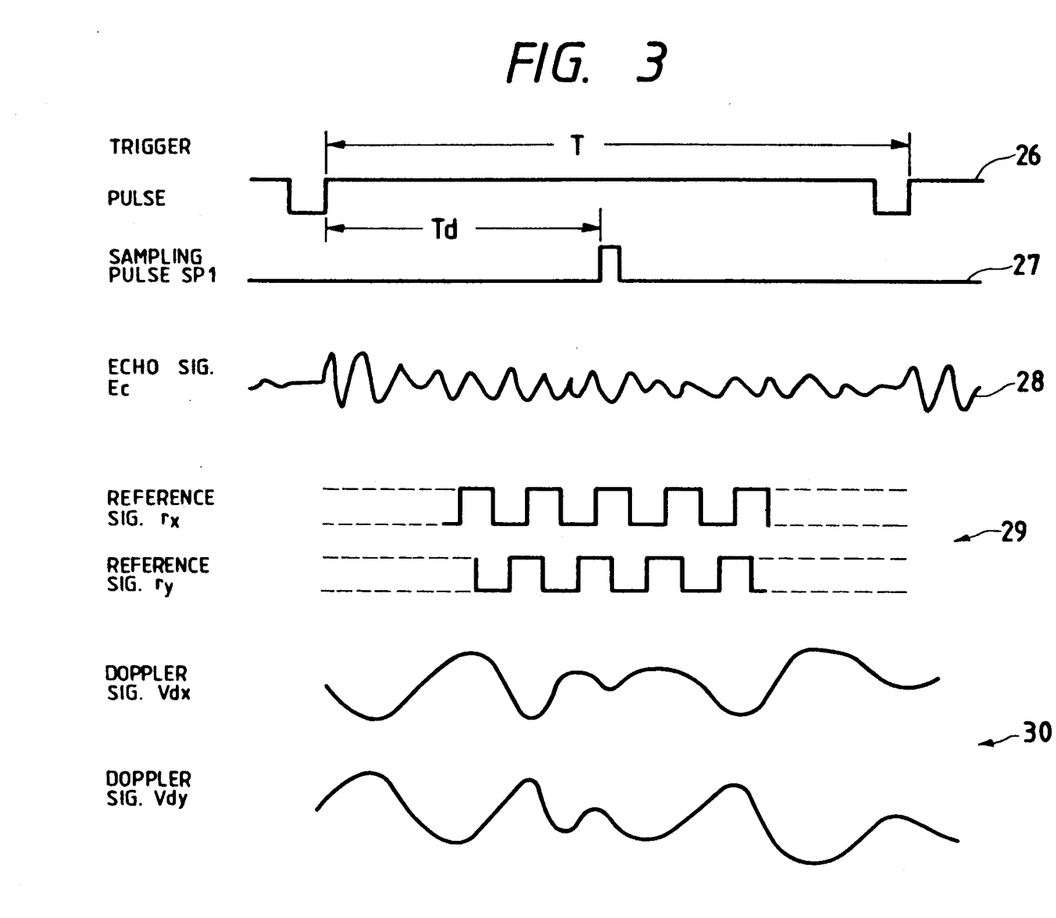
FIG. 3 shows waveforms for explaining operation of the first embodiment.
Figure 4:
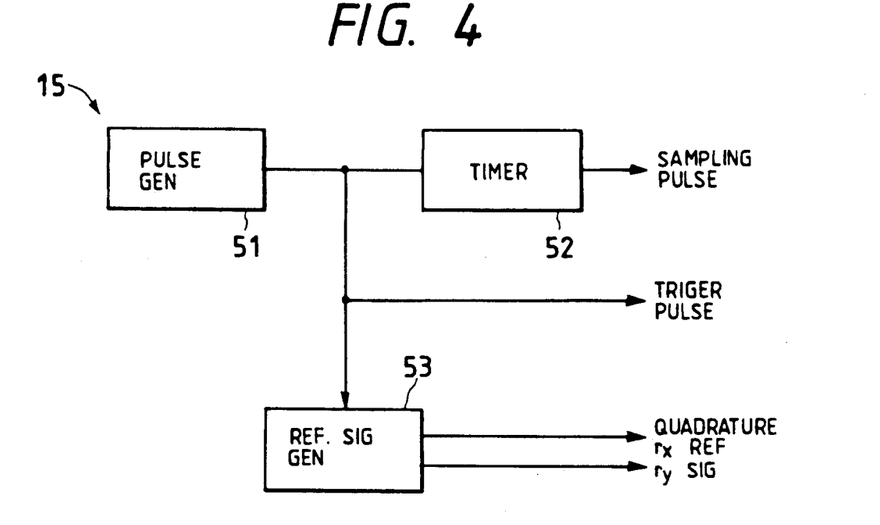
FIG. 4 is a block diagram of a signal generator of FIG. 1.
Figure 5:
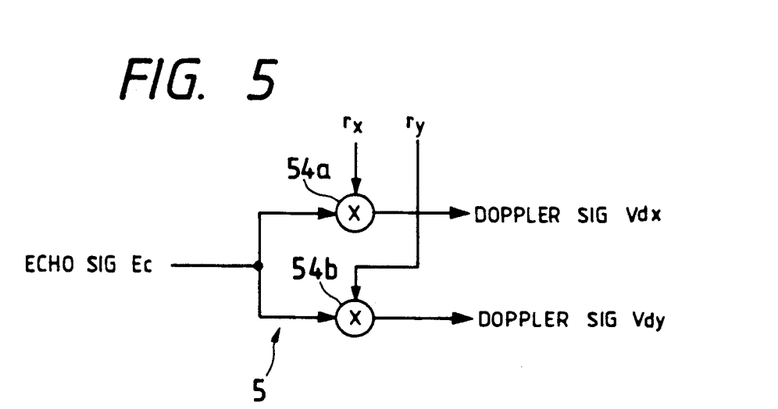
FIG. 5 is a block diagram of a Doppler signal detection circuit of FIG. 1.
Figure 6:
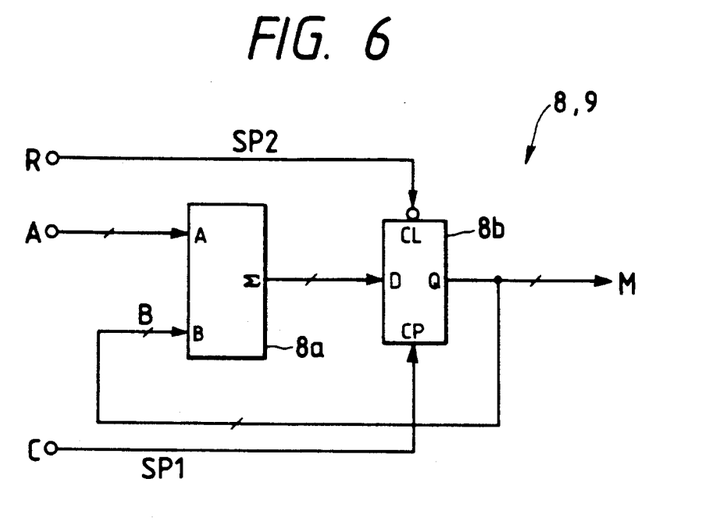
FIG. 6 is a block diagram of adding circuits of FIG. 1.

FIG. 4 is a block diagram of the signal generator 15. In FIG. 4, a pulse generator 51 generates trigger pulses applied to the drive circuit 4, a timer 52, and reference signal generator. As shown in FIG. 3, the trigger pulse is generated at every interval T. The timer 52 generates the first sampling clocks SP1 in response to trigger pulse with time delay Td. The reference signal generator 53 generates quadrature reference signals rx and ry in response to the trigger pulse, the quadrature reference signals having phase difference of 90° each other, as shown in waveforms 29. FIG. 5 is a block diagram of the Doppler signal detection circuit 5. In FIG. 5, the echo signal Ec from the probe 1 is applied to the multipliers 54a and 54b supplied with the quadrature reference signals rx and ry respectively for producing the Doppler signals Vdx and Vdy. FIG. 6 is a block diagram of the adding circuits 8 and 9. In FIG. 6, a full adder 8a adds A-input value to B-input value. A-input is responsive to an output of A/D converter 6 or 7. B-input responses to Q-output of a data latch 8b which is reset by the second sampling clock SP2 to zero at first. The data latch 8b stores D-input value from the adder 8a in response to the sampling clock SP1 through terminal C. At subsequent sampling clock SP1, the adder 8a adds the firstly added data to new incoming data from the A/D converter 6 or 7. This operation is repeated until next sampling clock SP2 arrives at the CL input of the latch 8b, so that values of Doppler signal are accumulated in the latch 8b until the second sampling clock SP2 reaches CL-input. When the sampling clock SP2 arrives at CL-input of the latch 8b, the latch 8b is reset. As described above, the mean value M is obtained from Q-output of the latch 8b, the number of averaging original sampling data of Doppler signal Vdx or Vdy being determined by frequency relationship between the sampling clocks SP1 and SP2, i.e., dividing ratio of the divider 14.

Hereinbelow will be described a second embodiment of an ultrasonic blood flow velocity detection apparatus.

Figure 7:
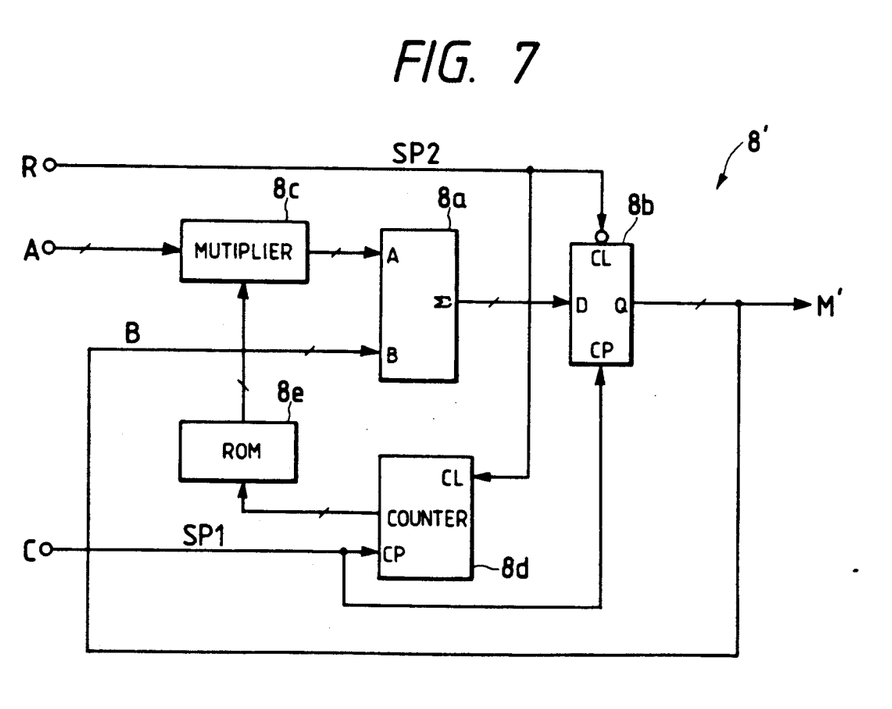
FIG. 7 is a block diagram of adding circuits of second embodiment.

General structure of the second embodiment of ultrasonic velocity detection apparatus is the same as that of the first embodiment apparatus. There is a difference between these embodiments in adding circuits 8, 9, and 8'. FIG. 7 is a block diagram of an adding circuit 8' which produces weighted mean values M'. In FIG. 7, an adder 8a adds A-input value to B-input value. A-input is responsive to an output of A/D converter 6 or 7. B-input responses to Q-output of a data latch 8b. Assuming coefficient from a ROM table 8e is one, a multiplier 8c sends a signal whose value is the same as the value applied therein, the signal being sent to the adder 8a. The adder 8a adds Doppler signal to an output of the latch 8b in the same way as first embodiment. The data latch 8b stores D-input value from the adder 8a in response to the sampling clock SP1 through terminal C and is reset by the second Sampling pulse SP2 applied to CL-input thereof. Therefore, the added data is once held in the data latch 8b. The held data is applied to the B-input of the adder 8a, so that values of Doppler signal are accumulated in the latch 8b until the second sampling clock SP2 reaches CL-input. On the other hand, a counter 8d counts up the first sampling clocks SP1 and is reset by the second sampling clock SP2. The count indicates which data incoming to the adder 8b with respect to the second sampling clock SP2. Therefore, an output of the counter 8d is used as an address signal of the ROM table 8e which stores coefficients and outputs respective coefficients in accordance with count of the counter 8d. For example, the ROM table 8e stores coefficients 0.5, 1.0, 1.0, and 0.5. The coefficient from the ROM table is applied to the multiplier 8c. Thus, coefficients 0.5, 1.0, 1.0, and 0.5 are successively outputted in response to the sampling clock SP1 or address signal from the counter 8d. The multiplier 8d multiplies Doppler signal by the coefficient which varies with count of the address signal from the counter 8d. Therefore, an weight mean value M' is obtained from Q-output of the latch 8b, the number of coefficients is the same as that of averaging original sampling data of Doppler signal Vdx or Vdy. In other words, the divider can be replace with the counter 8d. Moreover CL-input of the counter 8d can be omitted if initial condition of the counter 8d is consistent with that of divider 14 and the full count of the counter is consistent with the dividing ratio of the divider 14.

Figure 9:
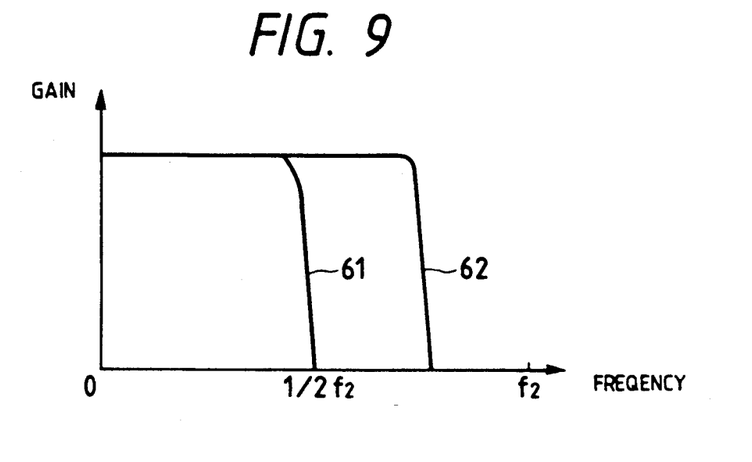
FIG. 9 shows frequency characteristic curves of weighting circuit of second embodiment.
Figure 10:
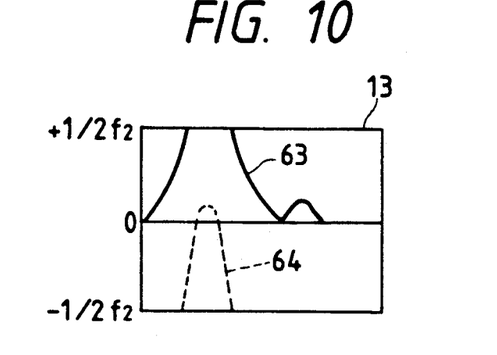
FIGS. 10 and 11 show indication by the second embodiment.
Figure 11:
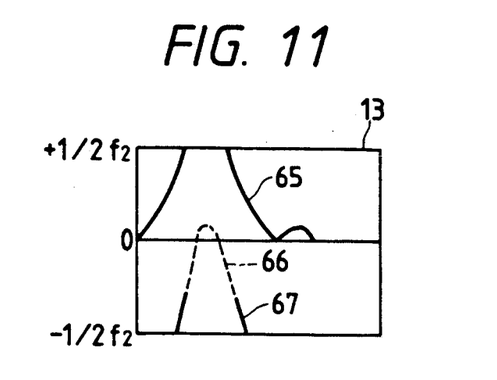

Weighting as shown in FIG. 7 has an effect equivalently obtained by a digital pass filter. Thus, if weighting is not performed, a Doppler signal whose shift frequency exceeds ±½·f2(frequency of sampling clock SP2) cannot be analyzed by the frequency analyzer 12 or displayed on the display 13. However, weighting enables analyzing and displaying such Doppler signal which causes overlapping, as shown in FIGS. 9-11. In FIG. 9, curve 61 shows a frequency characteristic of weighting circuit when all weighting coefficients are 1.0. In this case, a Doppler signal is indicated up to a half of second sampling clock frequency f2. On the other hand, when weighting coefficients are 0.5, 1.0, 1.0, and 0.5, the frequency characteristic is expanded as shown by curve 62. Frequency components of the Doppler signal exceeding ½·f2 are indicated or not indicated on the display 13, as shown FIGS. 10 and 11. Such components are indicated on the display 13, as shown by curve 67 of a solid line. The curve 67 is indicated a range between 0 to −½·f2. However, actual range is over ½·f2. On the other hand, when all coefficients are 1.0, such components are not indicated on the display 13, as shown by curve 64 of a dot line. Therefore, various display ranges necessary for diagnosis can be selected from several sets of coefficient tables.

What is claimed is:

1. An ultrasonic Doppler blood flow velocity detection apparatus comprising:
    (a) signal producing means for producing trigger pulses, a sampling clock signal having a given phase relation with said trigger pulses, and a pair of quadrature signals of a given frequency in response to said trigger pulses;
    (b) transducing means for transmitting ultrasonic waves in response to said trigger pulses and for receiving ultrasonic waves reflected by an ultrasonic-wave reflective object and converting the received ultrasonic waves into an electric echo signal;

(c) Doppler shift detection means responsive to said pair of quadrature signals and said echo signal for detecting Doppler shift; and (d) low-pass filter means for removing high frequency components from said Doppler shift by averaging time-different values of said Doppler shift in response to said sampling clock signal and said Doppler shift, thereby producing a signal indicative of flow velocity of said ultrasonic-wave reflective object.

2. An ultrasonic Doppler flow velocity detection apparatus as claimed in claim 1, wherein said low-pass filter means comprises:

(a) frequency dividing means responsive to said sampling clock signal for frequency-dividing said sampling clock signal;

(b) latching means responsive to the output of said dividing means for latching an input value; and (c) adding means responsive to said sampling clock signal, and an output of said frequency dividing means for adding a current value of said Doppler shift to a value for the input to said latching means to determine a total value of said plural values whose number is determined by relationship between said pulses and said output of said frequency dividing means.

3. An ultrasonic Doppler blood flow velocity detection apparatus as claimed in claim 2, further comprising bit-shift means responsive to an output of said latching means to obtain the average value of said plural values from said total value.

4. An ultrasonic Doppler blood flow velocity detection apparatus comprising:

(a) signal producing means for producing trigger pulses, a sampling clock signal having a given phase relation with said trigger pulses, and a pair of quadrature signals of a given frequency in response to said trigger pulses;

(b) transducing means for transmitting ultrasonic waves in response to said trigger pulses and for receiving ultrasonic waves reflected by an ultrasonic-wave reflective object and converting the received ultrasonic waves into an electric echo signal;

(c) Doppler shift detection means responsive to said pair of quadrature signals and said echo signal for detecting Doppler shift;

(d) low-pass filter means for removing high frequency components from said Doppler shift by averaging plural time-different values of said Doppler shift in response to said sampling clock signal and said Doppler shift, thereby producing a signal indicative of flow velocity of said ultrasonic-wave reflective object; and (e) weighting means responsive to an output of said Doppler shift detection means, and said sampling clock signal for weighting every value of said plural time-different values in accordance with predetermined weighting coefficients.

5. An ultrasonic Doppler blood flow velocity detection apparatus as claimed in claim 4, wherein said weighting means comprising:

(a) counting means responsive to said sampling clock for counting said sampling clock;

(b) storing means responsive to an output of said counting means for generating said weighting coefficients; and (c) multiplying means response to said Doppler shift and an output of said storing means for multiplying said Doppler shift by said coefficient.

6. An ultrasonic Doppler blood flow velocity detection apparatus comprising:

(a) signal producing means for producing trigger pulses, a first sampling clock signal of frequency f1 having a given phase relation with said trigger pulses, and a pair of quadrature signals of a given frequency in response to said trigger pulses;

(b) transducing means for transmitting ultrasonic waves in response to said trigger pulses and for receiving ultrasonic waves reflected by an ultrasonic-wave reflective object and converting the received ultrasonic waves into an electric echo signal;

(c) Doppler shift detection means responsive to said pair of quadrature signals and said echo signal for detecting Doppler shift frequency fd; and (d) frequency dividing means for frequency-dividing said first sampling clock signal by N (where N is a natural number and N>0) to produce a second sampling clock signal of frequency f2, said N being selected in accordance with a measurement range of a flow velocity of said ultrasonic reflective object; and (e) low-pass filter means for removing high frequency components from said Doppler shift by averaging N-time-different values of said Doppler shift in response to said first and second clock signals, thereby producing a signal indicative of flow velocity of said ultrasonic-wave reflective object with an overlap developed in said echo signal reflected at said reflective object having a velocity such that said reflective object produces said Doppler shift frequency fd higher than f2 but lower than f1 suppressed.

* * * * *